United States Patent [19]
Wang et al.

[11] Patent Number: 5,221,445
[45] Date of Patent: * Jun. 22, 1993

[54] METHOD FOR DETERMINING IDENTIFICATION AND CONCENTRATION OF AN ATMOSPHERIC COMPONENT

[75] Inventors: Da Y. Wang, Lexington; Daniel T. Kennedy, Burlington, both of Mass.; Burton W. MacAllister, Jr., Hudson, N.H.

[73] Assignee: GTE Laboratories Incorporated, Waltham, Mass.

[*] Notice: The portion of the term of this patent subsequent to Jan. 14, 2009 has been disclaimed.

[21] Appl. No.: 339,458

[22] Filed: Apr. 17, 1989

[51] Int. Cl.$^5$ .................................. G01N 27/406
[52] U.S. Cl. ........................ 204/153.1; 204/426; 204/153.2; 204/153.22; 204/425
[58] Field of Search .................. 204/153.18, 421–429, 204/153.1, 153.2, 153.22

[56] References Cited
U.S. PATENT DOCUMENTS

| | | | |
|---|---|---|---|
| 2,773,237 | 12/1956 | Offutt et al. | 204/153.1 |
| 4,450,065 | 5/1984 | Yamada et al. | 204/425 |
| 4,769,124 | 9/1988 | Okada et al. | 204/408 |
| 4,770,760 | 9/1988 | Noda et al. | 204/426 |
| 4,909,072 | 3/1990 | Logothetis et al. | 204/426 |

*Primary Examiner*—T. Tung
*Attorney, Agent, or Firm*—J. Stephen Yeo

[57] ABSTRACT

Apparatus and method for determining the identity and concentration of a component in a test atmosphere having a known concentration of oxygen. At least one solid electrolyte oxygen sensor is used, with each sensor having a solid electrolyte wall in contact with, and interposed between, a first electrode and a second electrode. The first electrode is in communication with the test atmosphere. A first negative voltage is applied across the first and second electrodes of a sensor, causing electrochemical oxygen pumping and a first electric current to flow through the corresponding solid electrolyte wall. The first negative voltage is selected to cause the first electric current magnitude to be on a first current plateau. The magnitude of the first electric current is measured.

A second negative voltage is applied across the first and second electrodes of a sensor, causing electrochemical oxygen pumping and a second electrical current to flow through the corresponding solid electrolyte wall. The second negative voltage is selected to cause the second electric current magnitude to be on a second current plateau. The magnitude of said second electric current is measured.

A table correlating pairs of numbers representing various combinations of first and second electric current with corresponding identity and concentration of one or more components is provided. The measured first and second magnitudes of electric current are matched with the pairs of numbers in the table and the corresponding identity and concentration of one or more component is determined.

6 Claims, 11 Drawing Sheets

METHOD FOR DETERMINING IDENTIFICATION AND CONCENTRATION OF AN ATMOSPHERIC COMPONENT

INCORPORATION BY REFERENCE

U.S. patent application Ser. No. 07/198,028 filed 5/24/88 by Wang, MacAllister, and Kennedy for Gas Sensing Apparatus, now U.S. Pat. No. 4,897,174, assigned to the same assignee as this, is hereby incorporated by reference.

BACKGROUND OF THE INVENTION

This invention pertains to measurements of atmospheric components, and more particularly is concerned with such measurements using solid electrolyte sensors.

Solid electrolyte sensors are used extensively to monitor exhaust gases from engines and other combustion devices to determine the percentage of oxygen in the test atmosphere. From this measurement the efficiency of the combustion process can be derived. Reactive gases and water vapor can affect the accuracy of the oxygen reading. What has not been recognized until this invention is that this phenomenon, which is generally considered detrimental to measurements, can be utilized for determining the identity and concentration of a component in a test atmosphere having a known concentration of oxygen.

An object of the invention is to provide a method for determining the identity and concentration of a component in a test atmosphere having a known concentration of oxygen using at least one solid electrolyte oxygen sensor.

Another object of the invention is to provide apparatus using at least one solid electrolyte oxygen sensor for determining the identity and concentration of a component in a test atmosphere having a known concentration of oxygen.

SUMMARY OF THE INVENTION

Briefly, according to one aspect of the invention, there is provided means for determining the identity and concentration of a component in a test atmosphere having a known concentration of oxygen. At least one solid electrolyte oxygen sensor is used, with each sensor having a solid electrolyte wall in contact with, and interposed between, a first electrode and a second electrode. The first electrode is in communication with the test atmosphere. A first negative voltage is applied across the first and second electrodes of a sensor, causing electrochemical oxygen pumping and a first electric current to flow through the corresponding solid electrolyte wall. The first negative voltage has a magnitude to cause the first electric current magnitude to be on a first current plateau. The magnitude of the first electric current is measured.

A second negative voltage is then applied across the first and second electrodes of a sensor, causing electrochemical oxygen pumping and a second electrical current to flow through the corresponding solid electrolyte wall. The second negative voltage has a magnitude to cause the second electric current magnitude to be on a second current plateau. The magnitude of the second electric current is measured.

A table correlating pairs of numbers representing various combinations of first and second electric currents with the corresponding identity and concentration of one or more components is provided. The measured first and second magnitudes of electric current are matched with the pairs of numbers in the table and the corresponding identity and concentration of one or more component are determined.

DETAILED DESCRIPTION OF THE INVENTION

Figure 1:
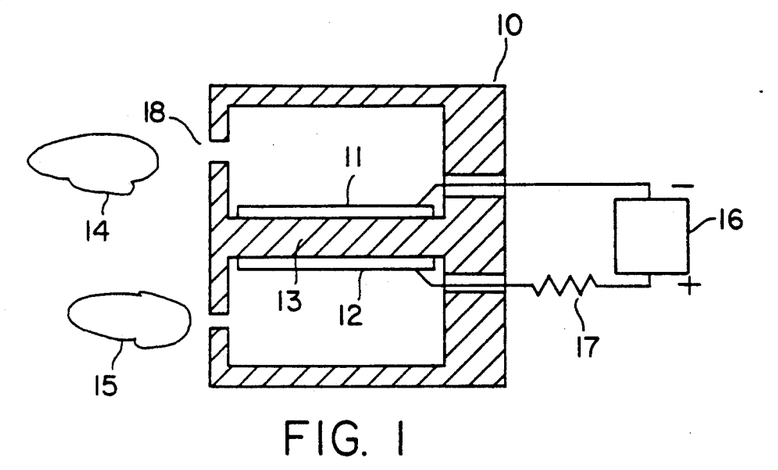
FIG. 1 illustrates, in schematic form, an oxygen sensor 10 suitable for practicing the invention.

FIG. 1 illustrates, in schematic form, an oxygen sensor 10 suitable for practicing the invention. Sensor 10 includes a pair of electrodes 11, 12 disposed on opposite sides of a solid electrolyte wall 13. Each electrode can be a layer of metal, e.g. platinum, or an electrically conducting ceramic deposited upon a surface of the solid electrolyte. The solid electrolyte can be any oxygen conducting material, preferably yttria or calcia-stabilized zirconia, or similarly doped ceria. At least one electrode 11, hereinafter called the first electrode, is exposed to the gaseous medium to be tested, referred to as test atmosphere 14. Details of one such a sensor are given by U.S. patent application Ser. No. 07/198,028 filed 5/24/88 by Wang, MacAllister, and Kennedy for Gas Sensing Apparatus.

To practice the method of the present invention, the test atmosphere should contain a known percentage of oxygen and may be air with an unknown component such as a reactive gas or water vapor. The purpose of the method is to determine the identity and concentration of the unknown component. The second electrode 12 is exposed to a second gaseous medium 15 which may be the test atmosphere or a separate reference atmosphere. When a sufficient negative voltage is applied between the first and second electrodes 11, 12, oxygen is diffused or "pumped" from atmosphere 14 through the solid electrolyte wall 13 to the gaseous medium 15. This voltage is called pumping voltage and is provided by a pumping voltage source 16.

In response, electric current will flow through solid electrolyte wall 13. This current is called the oxygen limiting current. The oxygen limiting current may be determined by measuring the voltage across a resistor 17 in series with the pumping voltage source 16 and the sensor. In conventional oxygen sensor measurements, the current is a function of the concentration of oxygen in the test atmosphere.

Figure 2:
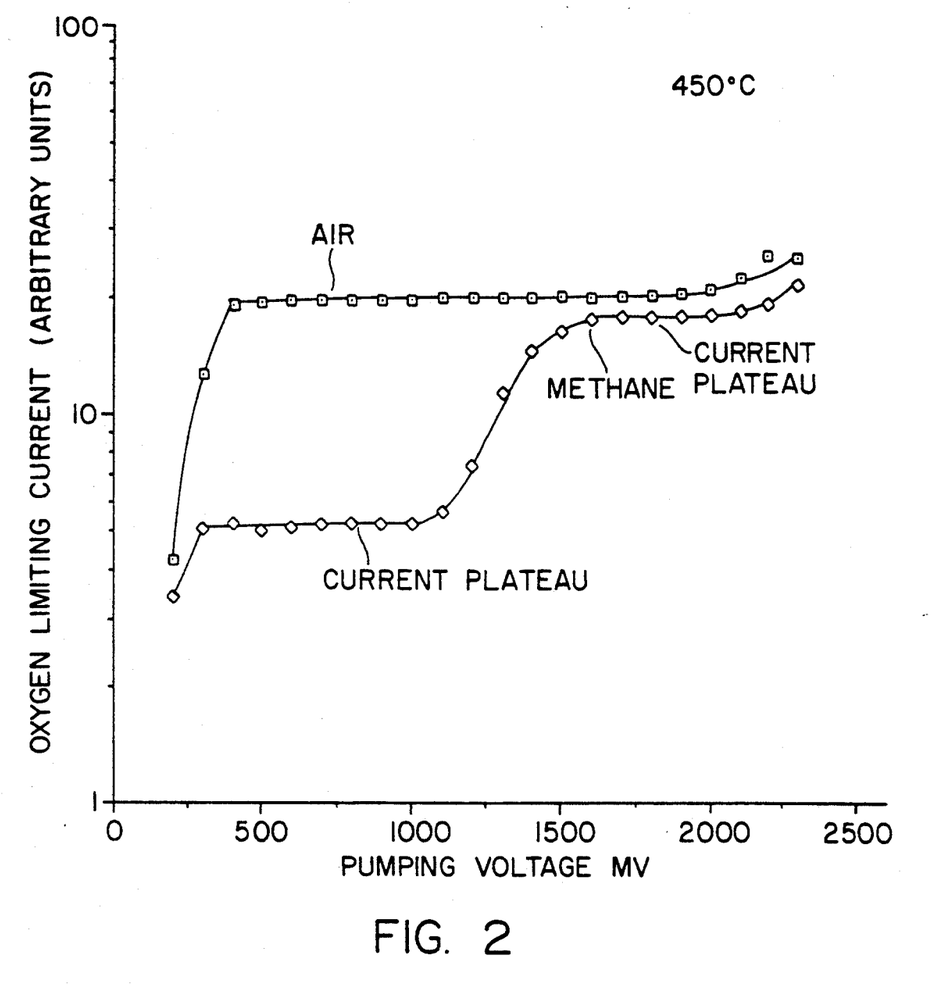
FIG. 2 has two curves, one curve illustrating that the saturated limiting current for air is on one plateau over a range of pumping voltages, and another curve illustrating that the saturated limiting current for methane has two plateaus over a range of pumping voltages.

A physical barrier 18, such as a small aperture or a gas permeable membrane, is provided between the surface of electrode 11 and test atmosphere 14 for limiting the diffusion of gas from the test atmosphere 14 to the first electrode 11 in such a way that for a wide range of pumping voltages the oxygen limiting current is at its saturation level, i.e., nearly constant as the pumping voltage is varied over a range. This phenomenon is illustrated by the top curve of FIG. 2 where the saturated limiting current for air is on a plateau for a pumping voltage between 450 mV and 2000 mV at a temperature of 450° C. Below 450 mV the limiting current is not saturated and the current drops. At pumping voltages above 2000 mV the solid electrolyte is reduced and the current rises.

An important property of such oxygen sensors is that with the presence of a reactive gas or fully oxidized gas such as water vapor in the test atmosphere, the electric current flowing though the solid electrolyte wall is approximately constant for two ranges of pumping voltages if all other parameters such as test atmospheric component concentration and temperature remain constant. For each of the two ranges that the current is approximately constant, the current is said to be on a saturated limiting current plateau. This is illustrated by the bottom curve of FIG. 2 which shows the two current plateaus of six percent methane in air. The mechanisms involved include gas absorption, gas diffusion, catalytic reactions, and oxygen reduction.

The lower of the two plateaus occurs because at lower pumping voltages, the presence of a reactive gas or water vapor in the test atmosphere will lower the amount of oxygen electrochemically pumped though the solid electrolyte wall, and therefore limit the corresponding electric current. The higher the concentration of reactive gas or water vapor in the test atmosphere, the lower will be the saturated limiting current plateau. The reason is that, in the case of a reactive gas, at lower pumping voltages the gas catalytically reacts with oxygen at the electrode. In the case of a fully oxidized gas, the oxygen concentration of the test gas is diluted by the oxidized gas.

Figure 3:
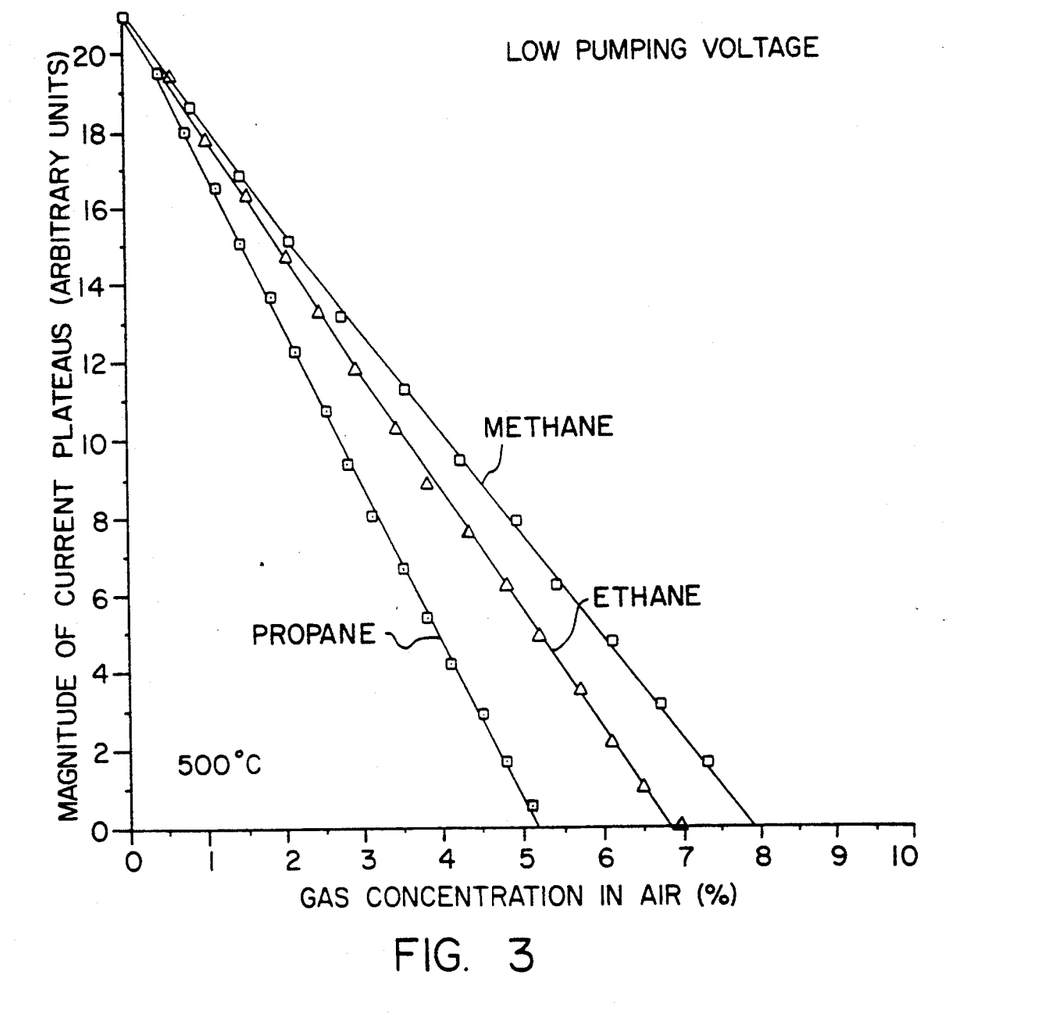
FIG. 3 shows how the magnitude of the lower plateau varies for different concentrations of methane, ethane, and propane in air.

The level or magnitude of the lower plateau depends upon the identity and concentration of the reactive gas in the test atmosphere, as seen in FIG. 3 for various mixtures of air and the alkane gases methane, ethane, and propane.

Figure 4:
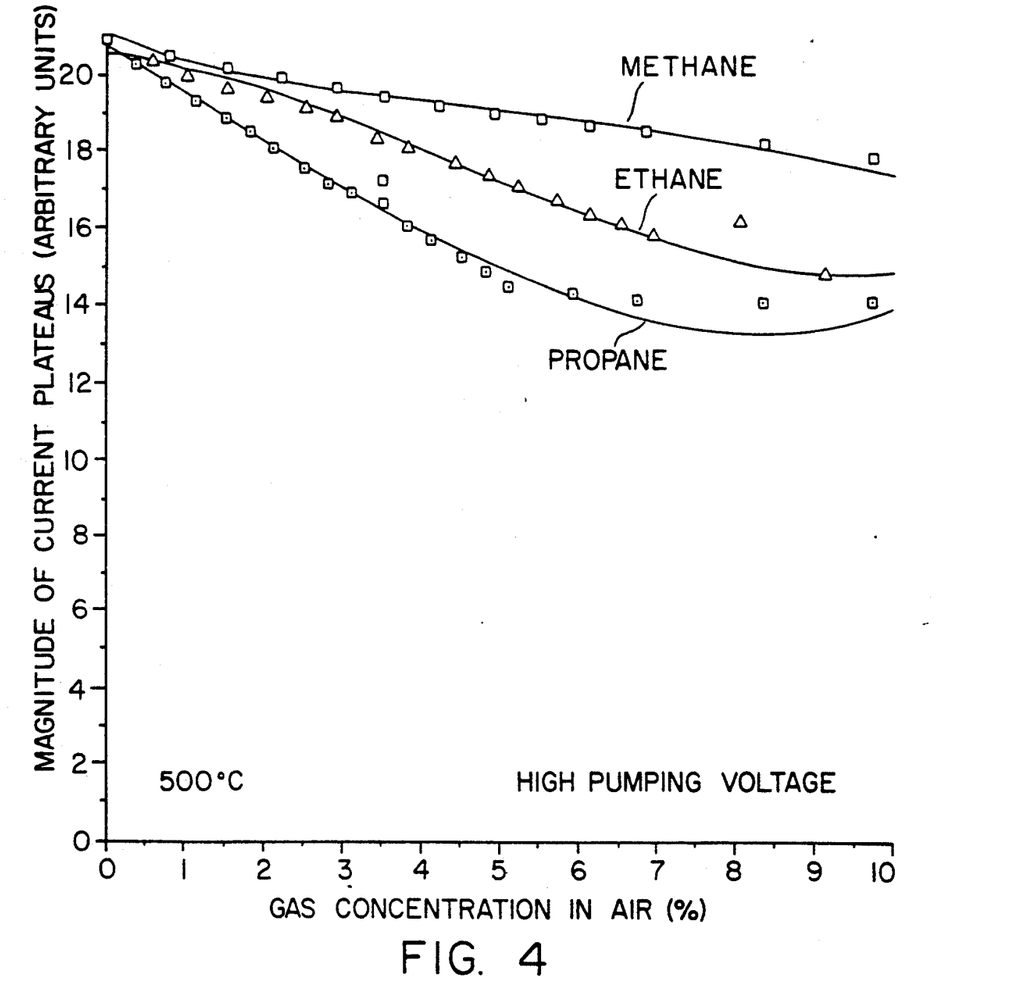
FIG. 4 shows how the magnitude of the higher plateau varies for the same concentrations of methane, ethane, and propane in air as in FIG. 3.

The higher of the two plateaus occurs because at higher pumping voltages the catalytic reaction involving the gas is stopped electrochemically or the fully oxidized gas becomes dissociated. The level or magnitude of the higher plateau also depends upon the identity and concentration of the reactive gas in the test atmosphere as seen in FIG. 4 for the same mixtures of air and methane, ethane, and propane seen in FIG. 3.

Figure 5:
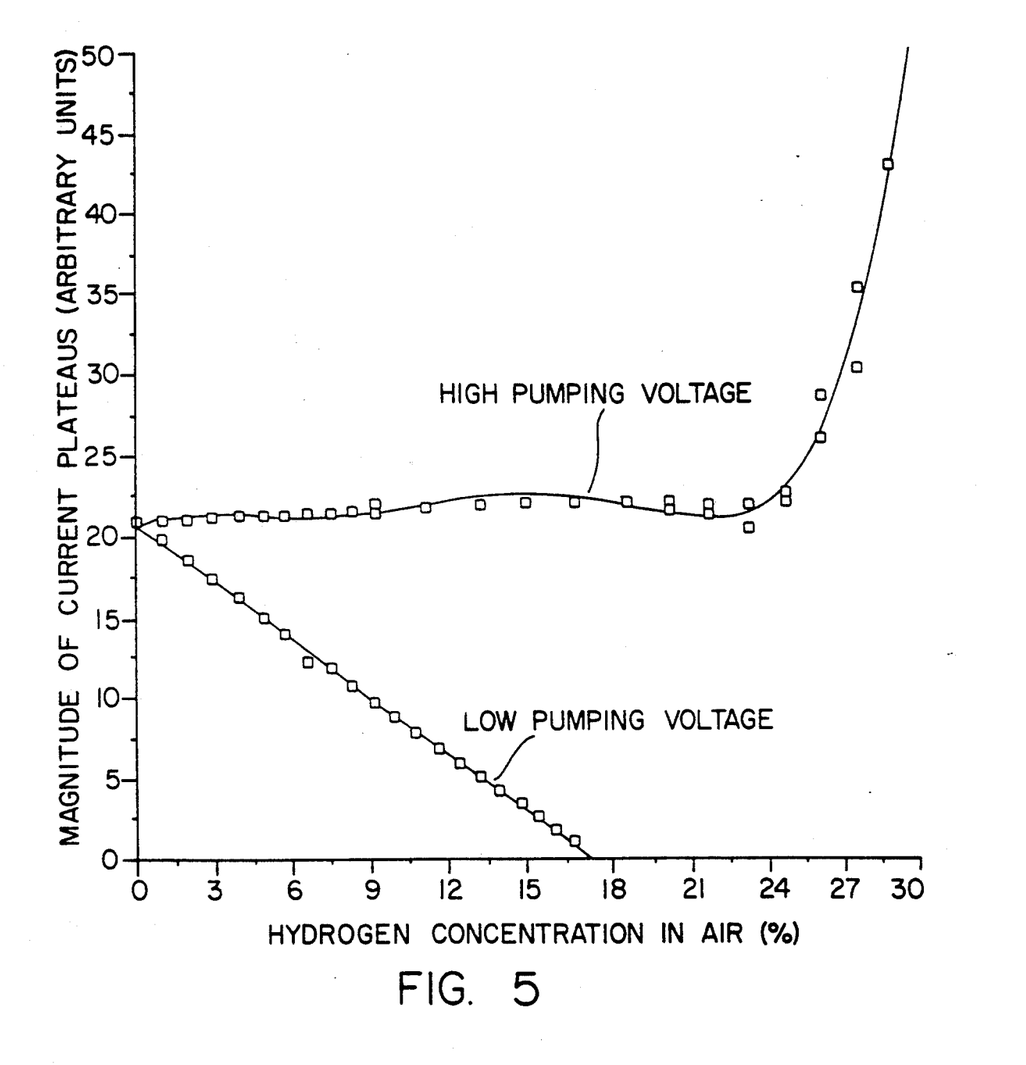
FIG. 5 presents the values of the higher and lower current plateaus for various concentrations of hydrogen in air.

The reactive gas can be almost any gas, including hydrogen. The values of the upper and lower current plateaus for various concentrations of hydrogen in air are shown in FIG. 5.

Figure 6:
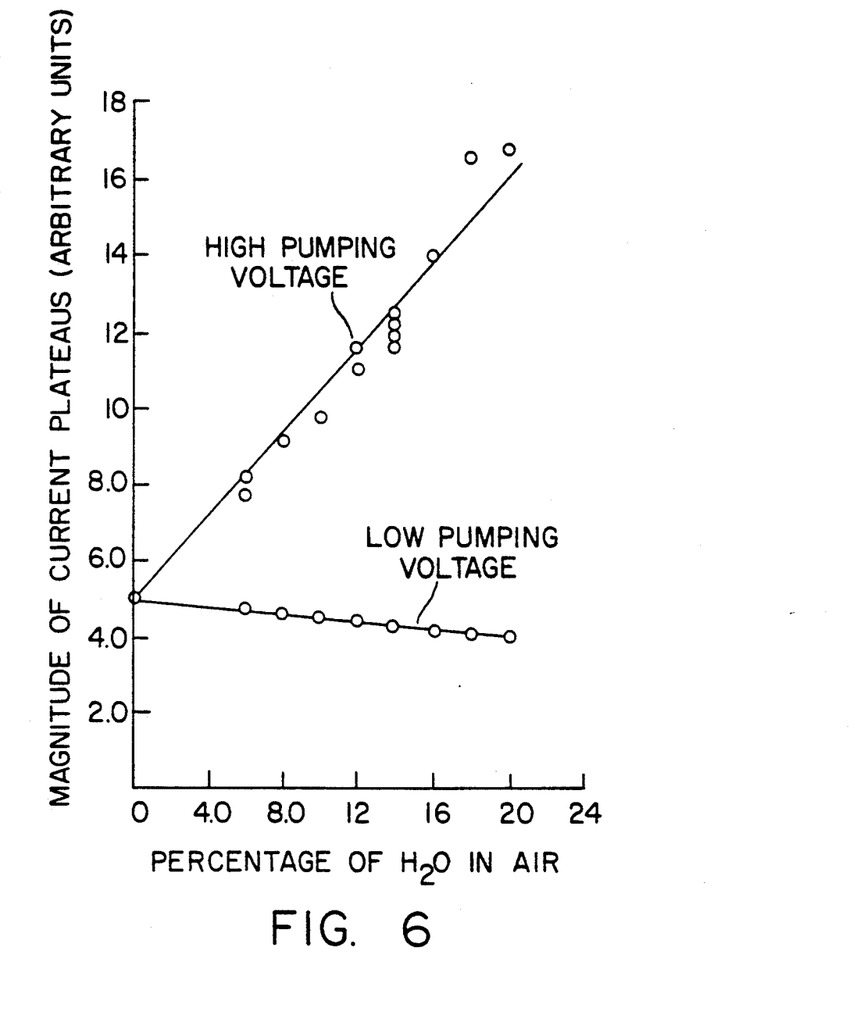
FIG. 6 shows the values of the higher and lower current plateaus for various concentrations of water vapor in air.

As previously indicated, the method is not limited to testing for reactive gases but may also be employed to measure water vapor concentration. The values of the upper and lower current plateaus for various concentrations of water vapor in air are shown in FIG. 6. At lower pumping voltages, water vapor physically dilutes the oxygen concentration. At higher pumping voltages, water vapor undergoes electrolysis.

As a common feature of all embodiments of the invention, the test atmosphere is tested at two pumping voltages. The lower pumping voltage is chosen to be a magnitude for the oxygen limiting current to be on a lower plateau. The higher pumping voltage is chosen to be a magnitude for the oxygen limiting current to be on a higher plateau. The magnitudes of the current on the two plateaus are measured to obtain a pair of values representing the oxygen saturated limiting currents. If all other parameters such as oxygen and temperature are constant, the two current levels are determined by the identity and concentration of the unknown component. The converse is also true. Both the identity and concentration of the unknown component are deduced from the two measured current levels.

Figure 7:
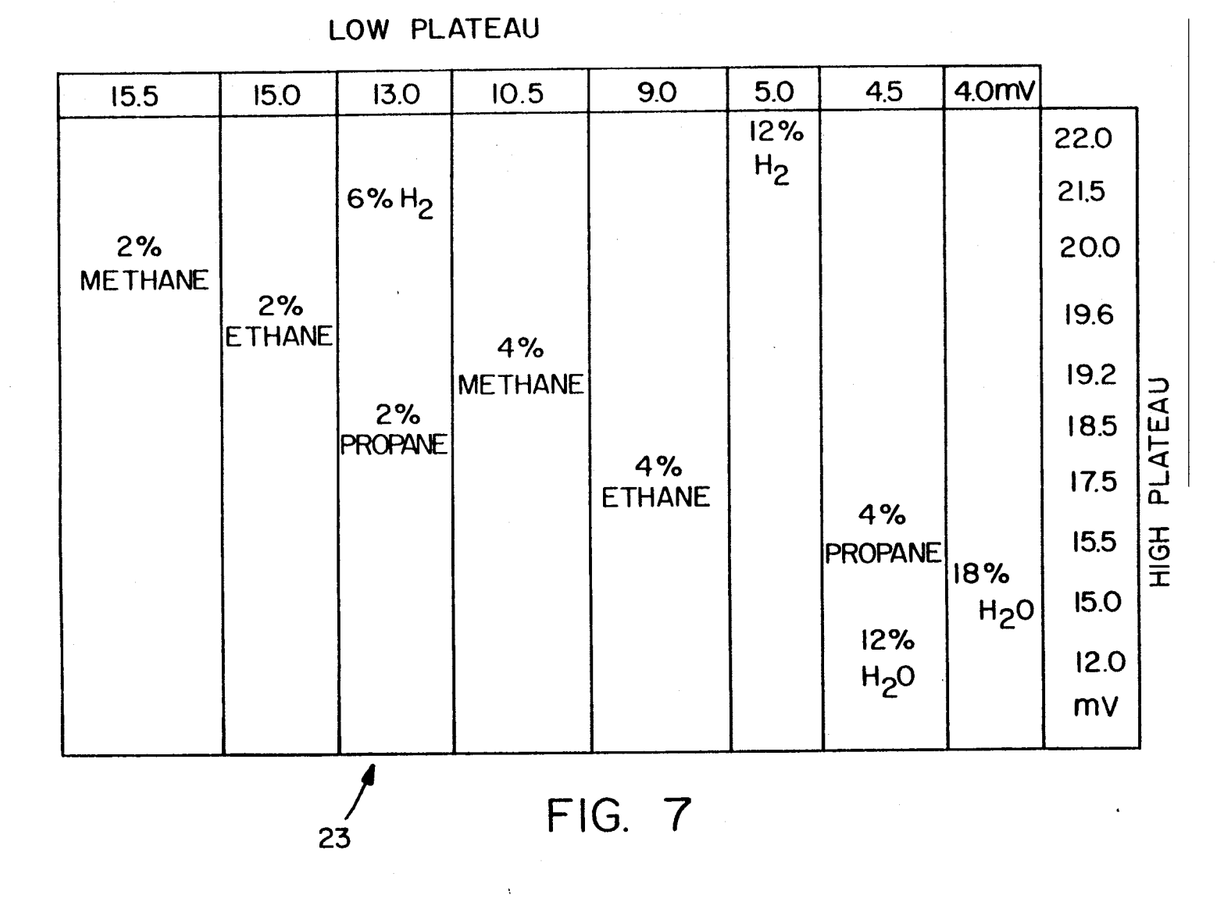
FIG. 7 is a table correlating concentration and identity of a component with high and low plateau values.

As another feature of the invention, there is provided a table containing pairs of numbers representing different combinations of current levels. As an example, a column may represent the value of a high plateau, while a row may represent the value of a low current plateau. For each pair of current levels, i.e. the intersection a of a column and row, the table provides the identity and concentration of the corresponding component. The data in the table are from measurements obtained from known concentrations of components, such as presented in FIGS. 3 to 6. An abridged table 23 is illustrated by FIG. 7. The dimensions of the table are in millivolts because the current is best determined by measuring the voltage drop across a series resistor.

Figure 8:
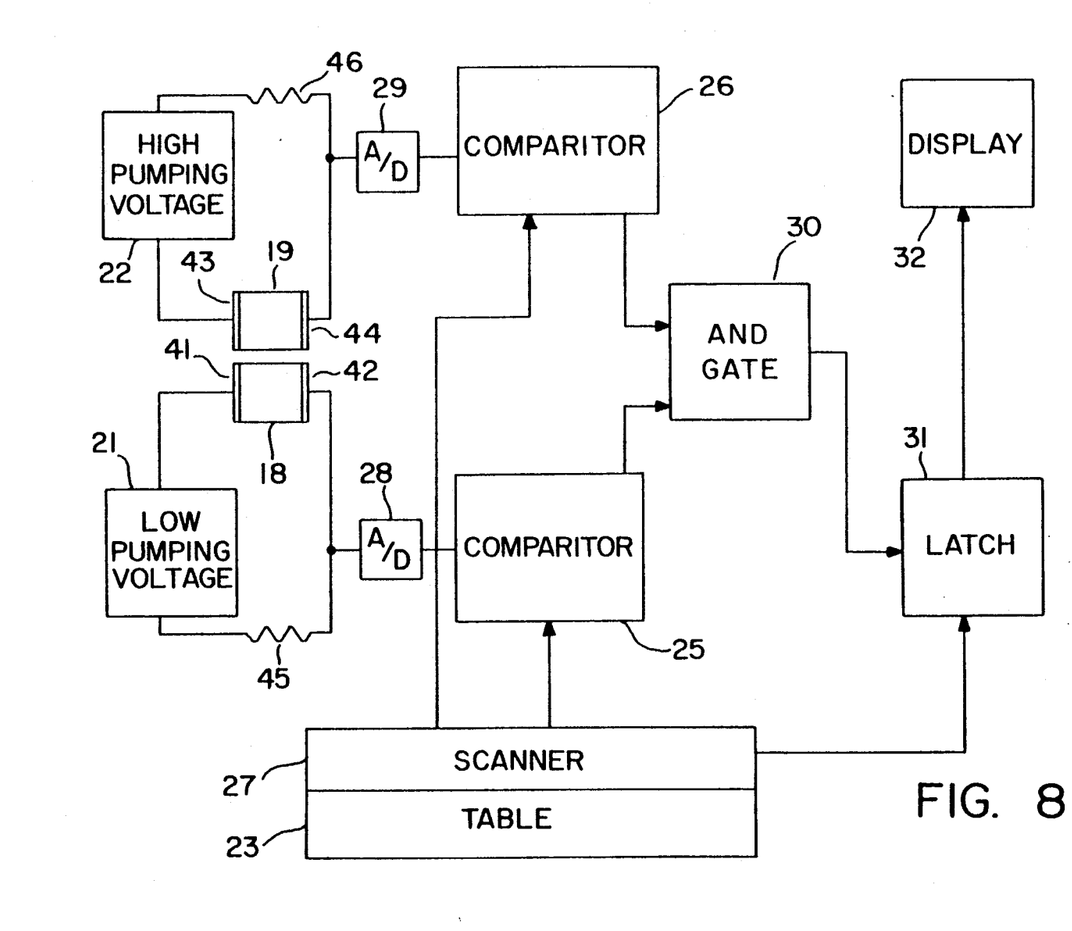
FIG. 8 is a block diagram of a first and preferred embodiment of apparatus contemplated by the invention.

A first preferred embodiment of the invention is seen in FIG. 8. Two sensors 18, 19 are provided.

Figure 9:
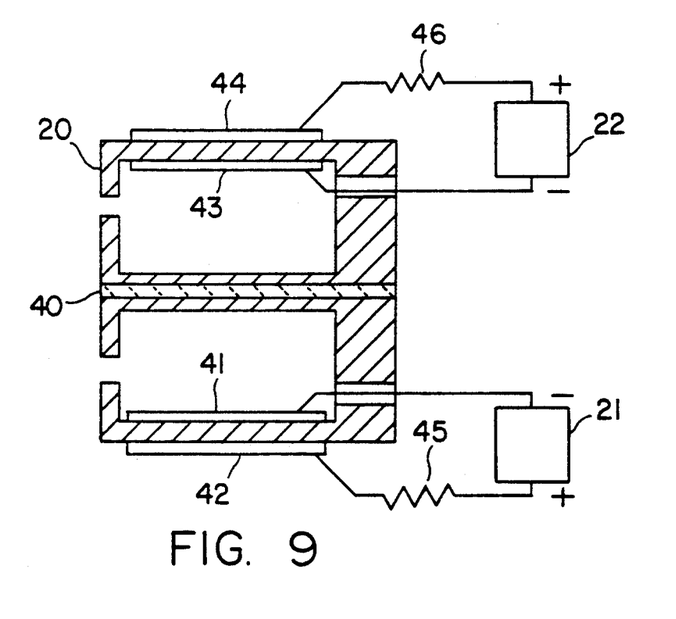
FIG. 9 is a schematic representation of two sensors combined in the same package.

Turning briefly to FIG. 9, it is seen that the two sensors 18, 19 may be packaged together in one unit 20. Unit 20 has two cavities made of solid electrolyte. The cavities are separated by a layer of insulating material 40, such as $Al_2O_3$, $ZrO_2$, or partially stabilized $ZrO_2$. Alternately, the sensors may be physically separated.

Returning to FIG. 8, the electrodes 41, 42 of one sensor 18 are coupled to a pumping voltage source 21 providing a voltage of a magnitude which causes the oxygen limiting current to be on a lower plateau. The electrodes 43, 44 of the other sensor, 19, are coupled to a pumping voltage source 22 providing a voltage of a magnitude which causes the oxygen limiting current to be on a higher plateau. Both sensors are in communication with a test atmosphere.

Two current readings are measured, e.g. by reading the voltage across corresponding series resistors 45, 46, and are compared to pairs of numbers representing different combinations of currents which are tabulated in a look-up table 23 such as seen in FIG. 7. The best match is obtained between the measured currents and the tabulated pairs, and the corresponding component identity and concentration is read from table 23.

The currents of sensors 18, 19 are measured and digitized by A/D converters 28, 29. The digitized signals representing the two currents are coupled to corresponding digital comparators 25, 26. Lookup table 23 containing pairs of numbers is scanned. Table 23 may be digitally stored in ROM and accessed by scanner 27. A digital signal representing the lower number of a pair is directed to the digital comparator 25 coupled to the sensor 18 with the lower current plateau. A digital signal representing the higher number of a pair is directed to the digital comparator 26 coupled to the sensor 19 with the higher current plateau. As the table 23 is scanned, the stored numbers are compared to the measured current values. The outputs of the two digital comparators 25, 26 are inputted to an AND-gate 30. When there is a match with both measured current values and a stored number pair both digital comparators 25 and 26 provide output signals which enables AND-gate 30, which in response closes a latch 31. Latch 31 is interposed between look-up table 23 and a display 32. When latch 31 is closed the component identity and concentration corresponding to the matched pair, and therefore the measure current values, is read from the table 23 and indicated upon display 32. Analog comparators can be used instead of digital if the A/D converters 28, 29 are eliminated and D/A converters used at the outputs of table 23.

Figure 10:
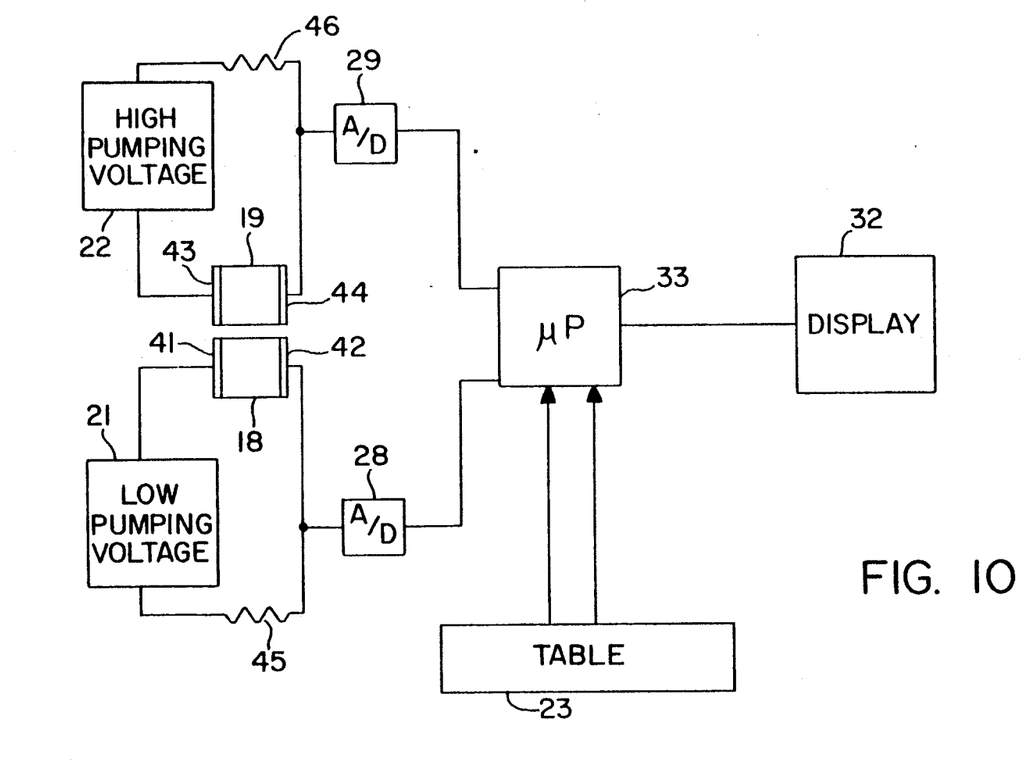
FIG. 10 shows apparatus similar to that of FIG. 8 with the comparisons between measured and table values made by a microprocessor.

In a variation of this embodiment, as shown in FIG. 10, the comparisons between measured and table values may be made by a microprocessor 33.

Figure 11:
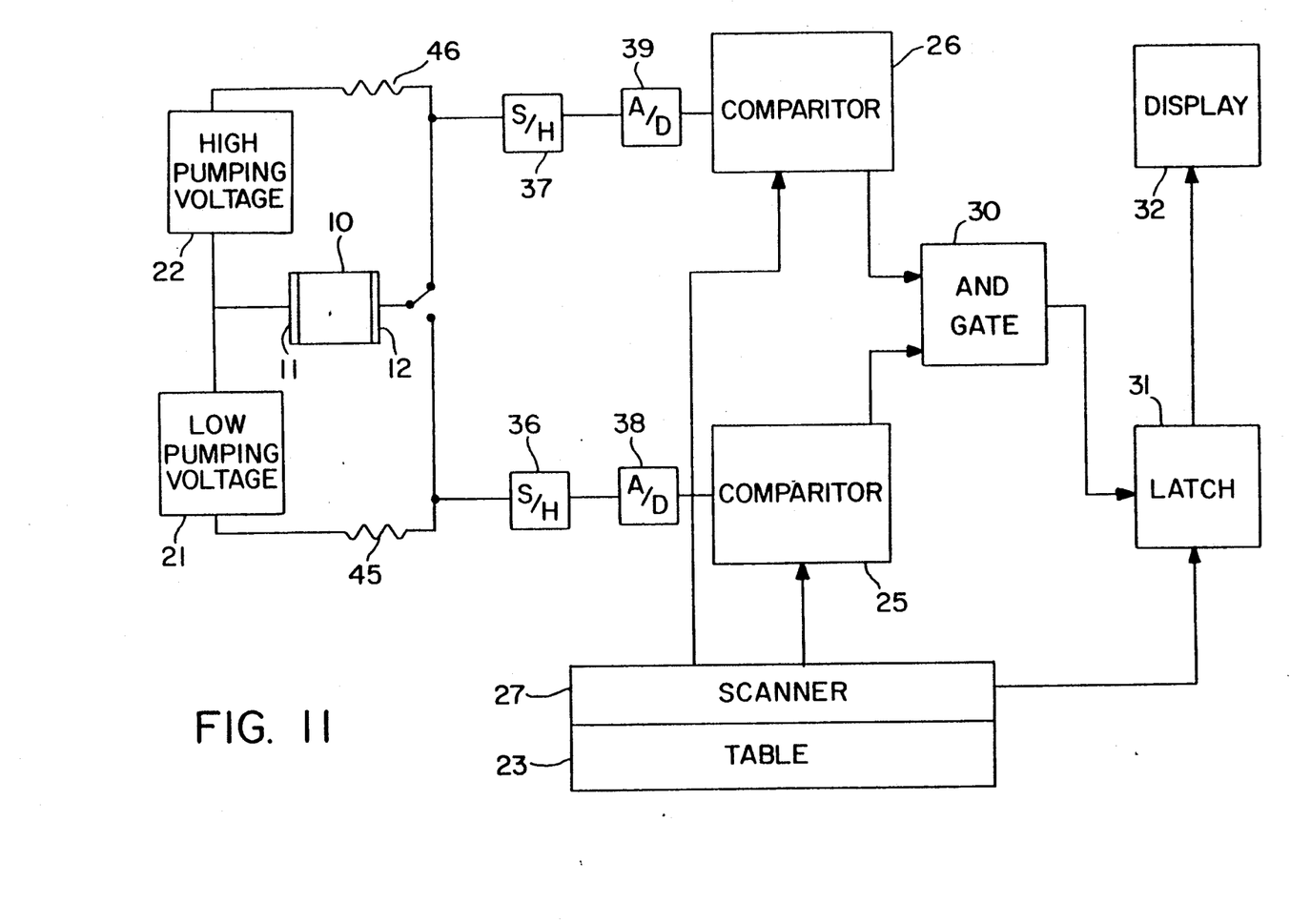
FIG. 11 represents an alternative embodiment using only one oxygen sensor.

In an alternative embodiment, seen in FIG. 11, one oxygen sensor 10 is used. Sensor 10 has a first electrode in communication with the test atmosphere and a second electrode in communication with the same test atmosphere or a reference atmosphere. High and low pumping voltages are applied sequentially across across the electrodes. The current reading for each voltage is observed and stored by sample and hold circuits 36, 37. When both current readings are obtained they are digitized by A/D converters 38, 39 and compared to the pairs of numbers tabulated in the look-up table 23 described above. As the table is scanned the best match is obtained between the measured currents and the tabulated pairs. The corresponding component identity and concentration is read from the table.

Figure 12:
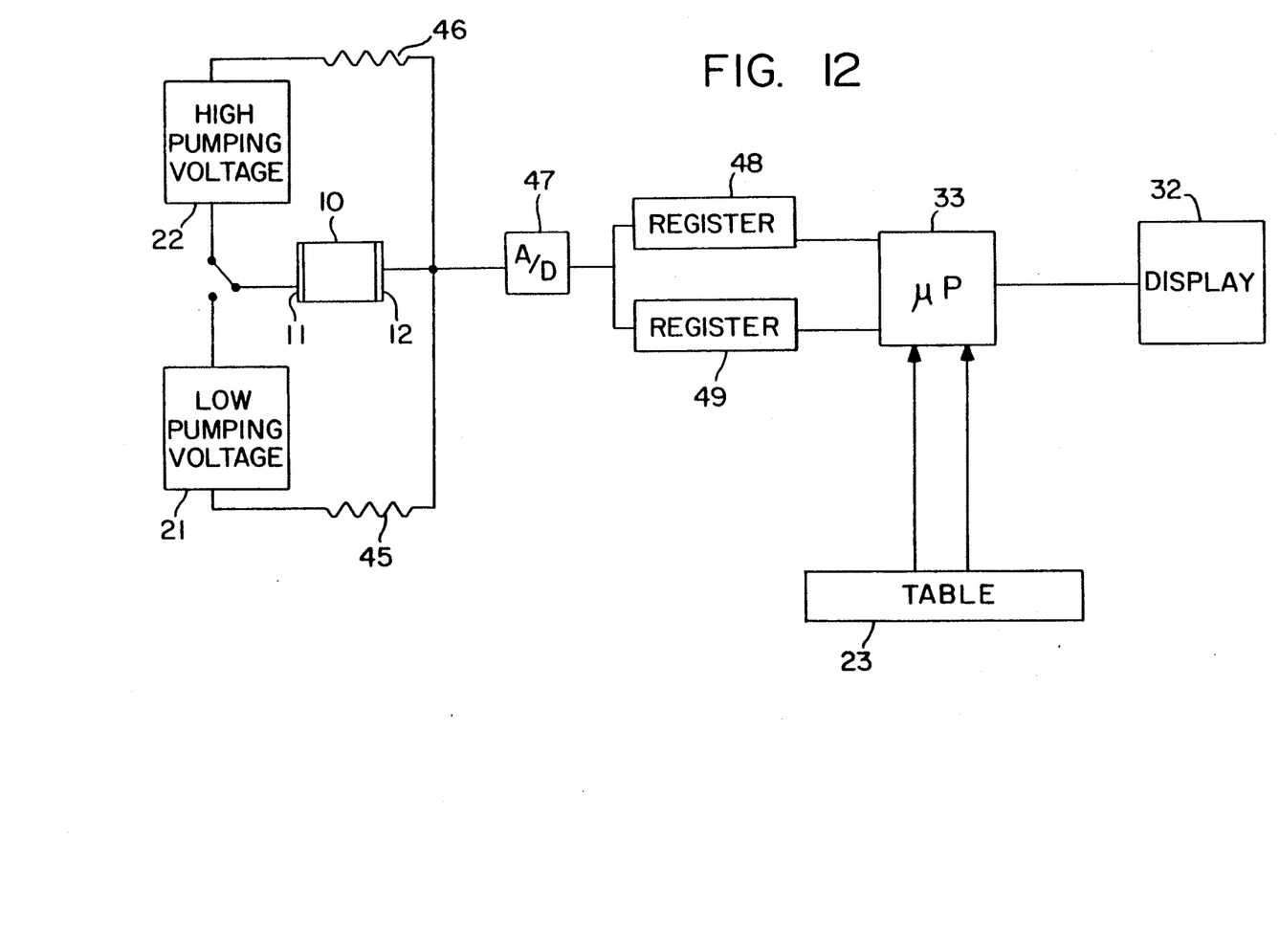
FIG. 12 shows apparatus similar to that of FIG. 11 with the comparisons between measured and table values made digitally by microprocessor.

In a variation of this embodiment, as show in FIG. 12, the comparisons between measured and table values may be made digitally by microprocessor 33. In this case, the measured current values are digitized by a/d convertor 47 and stored in buffer registers 48, 49.

The preferred embodiments of the invention and the the best mode of practicing it have been disclosed. With these teachings various modifications and variations will be apparent to those skilled in the art. Accordingly the scope of the invention is to be determined by the following claims and not by the specific examples given above.

What is claimed is:

1. A method of determining the identity and concentration of a component in a test atmosphere having a known concentration of oxygen, comprising the steps of:
   providing at least one solid electrolyte oxygen sensor, each sensor having a solid electrolyte wall in contact with, and interposed between, a first electrode and a second electrode, said first electrode in communication with said test atmosphere;
   applying a first negative voltage across first and second electrodes of a sensor, causing electrochemical oxygen pumping and a first electric current to flow through the corresponding solid electrolyte wall, said first negative voltage is of a magnitude to cause said first electric current to be on a first current plateau;
   measuring the magnitude of said first electric current;
   applying a second negative voltage across first and second electrodes of a sensor, causing electrochemical oxygen pumping and a second electrical current to flow through the corresponding solid electrolyte wall, said second negative voltage is of a magnitude to cause said second electric current to be on a second current plateau;
   measuring the magnitude of said second electric current;
   providing a table correlating pairs of numbers representing various combinations of first and second electric currents with corresponding identity and concentration of one or more components; and
   matching the measured first and second magnitudes of electric current with said pairs of numbers in said table and determining the corresponding identity and concentration of one or more component.

2. The method of claim 1 wherein said solid electrolyte wall is made of yttria or calcia-stabilized zirconia.

3. A method of determining the identity and concentration of a component in a test atmosphere having a known concentration of oxygen, comprising the steps of:
   providing a solid electrolyte oxygen sensor, said sensor having a solid electrolyte wall in contact with, and interposed between, a first electrode and a second electrode, said first electrode in communication with said test atmosphere;
   applying a first negative voltage across the first and second electrodes of said sensor, causing electrochemical oxygen pumping and a first electric current to flow through the solid electrolyte wall, said first negative voltage is of a magnitude to cause said first electric current to be on a first current plateau;
   measuring and storing a value representing the magnitude of said first electric current;
   applying a second negative voltage across first and second electrodes of said sensor, causing electrochemical oxygen pumping and a second electrical current to flow through the solid electrolyte wall, said second negative voltage is of a magnitude to cause said second electric current to be on a second current plateau;
   measuring and storing a value representing the magnitude of said second electric current;
   providing a table correlating pairs of numbers representing various combinations of first and second electric currents with corresponding identity and concentration of one or more components; and
   matching the values representing the measured first and second magnitudes of electric current with said pairs of numbers in said table and determining the corresponding identity and concentration of one or more component.

4. The method of claim 3 wherein said solid electrolyte wall is made of yttria or calcia-stabilized zirconia.

5. A method of determining the identity and concentration of a component in a test atmosphere having a known concentration of oxygen, comprising the steps of:
   providing first and second solid electrolyte oxygen sensors, each sensor having a solid electrolyte wall in contact with, and interposed between, a first electrode and a second electrode, said first electrode in communication with said test atmosphere;

applying a first negative voltage across first and second electrodes of the first sensor, causing electrochemical oxygen pumping and a first electric current to flow through the corresponding solid electrolyte wall, said first negative voltage is of a magnitude to cause said first electric current to be on a first current plateau;

measuring the magnitude of said first electric current;

applying a second negative voltage across first and second electrodes of the second sensor, causing electrochemical oxygen pumping and a second electrical current to flow through the corresponding solid electrolyte wall, said second negative voltage is of a magnitude to cause said second electric current to be on a second current plateau;

measuring the magnitude of said second electric current;

providing a table correlating pairs of numbers representing various combinations of first and second electric current with corresponding identity and concentration of one or more components; and matching the measured first and second magnitudes of electric current with said pairs of numbers in said table and determining the corresponding identity and concentration of one or more component.

6. The method of claim 5 wherein said solid electrolyte wall is made of yttria or calcia-stabilized zirconia.

* * * * *